United States Patent [19]
Yoshida et al.

[11] Patent Number: 5,922,209
[45] Date of Patent: Jul. 13, 1999

[54] PROCESS FOR DEACTIVATING OR DESTROYING MICROORGANISMS

[75] Inventors: Kanji Yoshida, 7-733-97, Izumi, Kumamoto-shi, Kumamoto-ken; Teruaki Sumioka, Kumamoto; Haitao Xu, Urawa, all of Japan

[73] Assignees: Remodeling 21 Co., Ltd., Tokyo; Kanji Yoshida, Kumamoto-ken, both of Japan

[21] Appl. No.: 08/967,887

[22] Filed: Nov. 12, 1997

Related U.S. Application Data

[63] Continuation of application No. 08/580,907, Dec. 29, 1995, abandoned.

[30] Foreign Application Priority Data

Sep. 8, 1995 [JP] Japan ................................. 7-251623

[51] Int. Cl.$^6$ .................................................. C02F 1/467
[52] U.S. Cl. ............................. 210/748; 210/764; 422/4; 422/22; 205/754; 205/755
[58] Field of Search ..................... 210/764, 748; 422/4, 22, 23; 205/742, 753–755, 760

[56] References Cited

U.S. PATENT DOCUMENTS

| | | | |
|---|---|---|---|
| 3,366,564 | 1/1968 | Allen ........................................ | 210/764 |
| 3,925,176 | 12/1975 | Okert ....................................... | 210/764 |
| 3,943,044 | 3/1976 | Fenn, III et al. ....................... | 210/764 |
| 4,179,347 | 12/1979 | Krause et al. ........................... | 210/764 |
| 4,402,318 | 9/1983 | Swartz ...................................... | 604/20 |
| 4,788,038 | 11/1988 | Matsunaga ............................... | 422/22 |
| 5,048,404 | 9/1991 | Bushnell et al. ........................ | 99/451 |
| 5,091,152 | 2/1992 | Thomas, Sr. ............................ | 422/23 |
| 5,304,486 | 4/1994 | Chang ..................................... | 435/287 |
| 5,685,994 | 11/1997 | Johnson .................................. | 210/748 |
| 5,695,650 | 12/1997 | Held ....................................... | 210/745 |

FOREIGN PATENT DOCUMENTS

| | | |
|---|---|---|
| 0468 478 A2 | 1/1991 | European Pat. Off. . |
| 28 15 030 | 10/1979 | Germany . |
| 32 33 282 | 3/1984 | Germany . |
| 2 246 955 | 2/1992 | Germany . |
| 2 273 048 | 6/1994 | Germany . |
| 637 422 | 7/1983 | Switzerland . |
| WO94/03399 | 2/1994 | WIPO . |

OTHER PUBLICATIONS

Patermarakis, G., et al., "Disinfection of Water by Electrochemical Treatment", *Water Research*, vol. 24, No. 12, pp. 1491–1496.

Abstract, "Ion Exchange Filter Device for Sterilizing and Removing Legionela Bacteria", Inventor: Shishido Kenji; Oct. 21, 1994.

Abstract, "Air Cleaner and Air Conditioner Equipped With This Cleaner", Inventor: Saito Toshihiko; Nov. 1, 1989.

Abstract, "Apparatus for Producing Sodium Hypochlorite", Inventor: Yuki Kuwako et al.; United Kingdom Appln. No. 2 202 551 A; Sep. 28, 1988.

Abstract, "Apparatus for Electrochemical Treatment of Water", Inventor: Vitold Mikhailovich Bakhir et al.; United Kingdom Appln. No. 2 274 113 A; Jul. 13, 1994.

Abstract, "Electrolytic Cell for Generating Sterilization Solutions Having Increased Ozone Content", Inventor: Baker et al.; U.S. Patent No. 5,316,740; May 31, 1994.

Abstract, "Electrolytic Cell for Generating Sterilization Solutions Having Increased Ozone Content", Inventor: Baker et al.; U.S. Patent No. 5,385,711; Jan. 31, 1995.

Abstract, "Device for Electroactivating Fluids and Preparations Consisting of Electroactivated Fluids", WO 90/15779; Dec. 27, 1990.

Abstract, "Compsn. for Disinfecting Water by Electro: Chlorination Process Crompises Alkaline Chloride(s) and a Chlorine Stabilising Agent Pref. Isocyanuric Acid"; EP 555598–A1.

*Primary Examiner*—Thomas G. Wyse
*Attorney, Agent, or Firm*—McDermott, Will & Emery

[57] ABSTRACT

Applying electrical energy to a microorganism through a liquid, gas or solid having electrical energy causes an increase in an electric charge in excess of the limit of intracellular and extracellular electrostatic capacity possessed by the microorganism, which results in an irreversible change in the microorganism cells and/or explosively destroys the border membrane of the microorganism cells.

16 Claims, No Drawings

PROCESS FOR DEACTIVATING OR DESTROYING MICROORGANISMS

This application is a continuation of application Ser. No. 08/580,907 filed Dec. 29, 1995 abandoned.

FIELD OF THE INVENTION

The present invention relates to a process for deactivating or destroying microorganisms, for the purpose of bacteriolysis, virolysis, disinfection or sterilization.

BACKGROUND OF THE INVENTION

Various processes have been developed and proposed to perform bacteriolysis, disinfection and sterilization by efficiently destroying microorganisms including bacteria such as *Pseudomonas aeruginosa* and *Escherichia coli* and other Eumycetes, and minute viruses. However, none of these known processes has adequately considered the properties of microorganisms. For example, electrochemical sterilization is premised on bringing the microorganisms into contact with an electrode surface or dielectric substance, to inhibit their biochemical reactions. The surface of a bacterium typically has a negative charge and is attracted to a positive electrode, and is destroyed by contact. However, when the number of bacteria increases, they exhibit a state in which protoplasm accumulates inside the bacteria, that protects the bacteria with protein. They thus effectively have an electrical shield. This causes a decrease in bactericidal function which makes maintenance and management of the electrodes susceptible to the occurrence of problems. As a result, practical application is correspondingly difficult.

SUMMARY OF THE INVENTION

This invention is based on a consideration of the mechanism by which microorganisms are destroyed. It has been found that, when bacteria are destroyed, they emit cytoplasm prior to contact with a positive electrode. Bacteria can be considered to be microcapacitors; their cell membrane is destroyed when they are subjected to an electric charge in an electric field, and that charge exceeds the electrostatic capacity.

A process for deactivating or destroying microorganisms, according to the present invention, involves applying electrical energy to microorganisms, in a charged medium (liquid, gas or solid). One aim is to increase the electrical charge in excess of the limit of intracellular and extracellular electrostatic capacity possessed by the microorganisms, and/or to promote intracellular and extracellular osmosis of the microorganisms. Another aim is to cause an irreversible change in the microorganism cells, or to explosively destroy the cell membrane.

The present invention thus offers the advantage of giving extremely high bactericidal, viricidal, disinfection and sterilization effects. Since any liquid, gas or solid can be used to apply electrical energy to microorganisms provided that it is effectively electrically-energised, the present invention offers the advantage of selecting from a very broad range of means for applying electrical energy, depending on the location where the microorganisms which are to be deactivated or destroyed are suspended or otherwise present.

DESCRIPTION OF THE INVENTION

The medium in which the microorganisms are treated is preferably charged water. Electrical energy is applied after placing microorganisms in this charged water. Such charged water may be, for example, any of charging water, battery water, functional water, electrolysis treatment water, high oxidation potential water, strongly acidic electrolytic regeneration aqueous solution, ionized water, non-ionized water and electrified water. Alternatively, the medium may be a gas having an electric charge, or a solid charge-accumulating substance.

One or more electrodes may also be used. The process in this case comprises applying current to a liquid containing the microorganism via an electrode and applying electrical energy. The microorganism are in a non-contact state with respect to the electrode. A specific non-contact process, for purifying water, and apparatus for use therein, are described and claimed in a copending Patent Application filed in the same name and on the same date. Alternatively, current supplied via the electrode may also be applied via an electrical medium or non-electrical medium.

In the specification, the term "microorganism" is used in the generic sense to refer to bacteria, including Eumycetes and minute viruses. The term "cell membrane" is used in the broad sense, and refers generically to the boundary membrane, external membrane; interfacial membrane, protoplasmic membrane or cell wall that separates the protoplasm of the cell from the outside.

The term "explosively destroying" as used herein refers directly to the states where strong membrane contraction occurs, the cell membrane having high strong elasticity, such that the cell contents (protoplasm) spray out and scatter radially in all directions; where the cell membrane has low elasticity and the internal pressure of the cell is high, such that local destruction of the cell membrane occurs, causing tranlational spraying with little peripheral scattering; or where the cell membrane has weak elasticity and external pressure is relatively low, such that translational spraying and peripheral scattering occur. The same term is also used in the broad sense, to refer generically to destruction, including turgor pressure destruction as well as lysis, dehydration, coagulation, melting, perforation and so forth, which are typical phenomena of bacterial destruction.

The term "charged water" is used herein to refer generically to charging water, battery water, functional water, electrolysis treatment water, high oxidation potential water, strongly acidic electrolytic regeneration aqueous solution, ionized water, non-ionized water or electrified water. The phrase "applying current" is not limited to the application of current via a conductive medium, e.g. a solution of a conductive substance such as NaCl, but also Includes the application of current via a liquid that is not generally supposed to be conductive, such as purified water. It has been confirmed that when current is applied after viable microorganisms are suspended in purified water, a current is obtained that is smaller than that in the conductive medium. This is apparently the result of a jumping conductivity effect (a type of non-electrical medium current flow) that exists between microorganisms, by which microorganisms form a constant flow in the direction of the positive electrode.

The term "osmosis" refers to the phenomenon of water in solution moving towards the higher concentration side when divided by a water-permeable solute-impermeable membrane. If the osmotic pressure is increased, it causes destruction of the cell membrane. The term "irreversible change" is used to refer generically to states in which the cell membrane inhibits the transport of substances, the cell membrane itself is changed or modified, or the protoplasm is changed or modified.

The following Examples illustrate the invention. In each, five microorganisms, i.e. *Staphylococcus aureus, Escheri-* chia coli, *Pseudomonas aeruginosa*, Candida and influenza virus, were tested.

EXAMPLE 1

Each of the five microorganisms was independently suspended in 0.01 ml purified water or tap water supplied by pipette, followed by dropwise addition of 0.01 ml drops of high oxidation potential water. The state of the microorganisms, In the form of a three-dimensional layer, was investigated using apparatus having a final maximum magnification factor of 4500×, consisting of an inverted system microscope IX-70 (manufactured by Olympus) equipped with a differential interference device and combined with a 355 mm (14 inch) monitor (with CCD). It was found that 70% of the microorganism cells ruptured and became debris after 1-drop addition, 80% after 2-drop addition and 99% after 3-drop addition, for all the five microorganisms listed above. Moreover, the amount of debris increased when 4 drops were added, and nearly 100% of the microorganisms cells exhibited a state of destruction when the final, 5th drop was added.

*Pseudomonas aeruginosa* is considered to be more resistant than the other microorganisms. It is worth noting that the cells of this microorganism were destroyed in the same manner as the other microorganisms listed above. Although it was difficult to visually recognize destruction of the border of Candida cells since they inherently do not move, deactivation or destruction of Candida could be confirmed since the oscillation of nearly all microorganisms present had stopped. In addition, during addition of the first three drops, some of the microorganisms had stopped moving but were not yet destroyed. In a very few cases, some microorganisms exhibited a slight degree of buoyancy.

EXAMPLE 2

Each of the five microorganisms was independently suspended in 0.01 ml purified water and in 0.01 ml tap water was added. Electrical energy of 0.2–0.3 mA:12 V and 0.5 mA:12 V was applied to the purified water and to the tap water via platinum electrodes. The cell membranes in 99% of the microorganisms were found to be ruptured.

EXAMPLE 3

Each of the five microorganisms was independently suspended in 0.01 ml purified water. A discharge tube was brought near the preparations, and the ionized gas generated around the discharge tube was allowed to act on the preparations. It was found that the cell membranes in 99% of the microorganisms had ruptured. It was thus confirmed that the intended deactivation or destruction was effected without making contact with the microorganisms.

EXAMPLE 4

Each of the five microorganisms was independently suspended in 0.01 ml purified water. A very small amount of carbon powder was sprinkled on the preparations. It was found that the cell membranes in 99% of the microorganisms had ruptured.

Similar results were obtained when electrostatically-charged polymer powder was used instead of the carbon powder. Further, when electrostatically-charged carbon powder was applied to dried microorganisms which can be wet-cultured, the degree to which those dried microorganisms could be cultured was extremely low.

We claim:

1. A process for deactivating or destroying microorganisms, comprising the steps of:
   suspending the microorganisms in a medium; and
   applying electrical energy to the medium to subject the microorganisms to an electric charge, wherein said electrical energy is sufficient to deactivate or destroy the microorganisms and wherein said electrical energy is applied via means other than an electrode.

2. The process of claim 1, wherein said medium is a liquid or gas.

3. The process of claim 1, wherein the electric charge is in excess of the limit of intracellular and extracellular electrostatic capacity possessed by the microorganisms.

4. The process of claim 1, wherein the electric charge promotes intracellular and extracellular osmosis of the microorganisms.

5. The process of claim 1, wherein said electrical energy is applied via a charged water, an electrically charged gas, or a solid charge accumulating substance.

6. The process of claim 5, wherein said charged water is selected from the group consisting of charging water, battery water, functional water, electrolysis treatment water, high oxidation potential water, strongly acidic electrolytic regeneration aqueous solution, ionized water, non-ionized water and electrified water.

7. The process of claim 5, wherein said electrically charged gas is generated around a discharge tube.

8. The process of claim 5, wherein said solid charge accumulating substance is selected from the group consisting of electrostatically charged carbon powder and electrostatically charged polymer powder.

9. The process of claim 1, wherein said medium is conductive.

10. The process of claim 1, wherein said medium is non-conductive.

11. A process for deactivating or destroying microorganisms, comprising the steps of:
    suspending the microorganisms in a liquid medium; and
    applying electrical energy to the medium to subject the microorganisms to an electric charge via an electrode that contacts no microorganisms, wherein said electrical energy is sufficient to deactivate or destroy the microorganisms.

12. The process of claim 11, wherein the electric charge is in excess of the limit of intracellular and extracellular electrostatic capacity possessed by the microorganisms.

13. The process of claim 11, wherein the electric charge promotes intracellular and extracellular osmosis of the microorganisms.

14. The process of claim 11, wherein said medium is conductive.

15. The process of claim 11, wherein said medium is non-conductive.

16. The process of claim 11, wherein said electrical energy is applied via a means selected from the group consisting of a charged water, a gas having an electrical charge, and a solid charge-accumulating substance.

* * * * *